United States Patent [19]

Grandy

[11] Patent Number: 4,641,968
[45] Date of Patent: Feb. 10, 1987

[54] MOBILE SPECTROMETRIC APPARATUS

[75] Inventor: Mark E. Grandy, Maynard, Mass.

[73] Assignee: Baird Corporation, Bedford, Mass.

[21] Appl. No.: 682,155

[22] Filed: Dec. 17, 1984

[51] Int. Cl.[4] ............................................. G01J 3/30
[52] U.S. Cl. ............................ 356/313; 315/209 CD; 350/582
[58] Field of Search ................ 356/313; 315/209 CD, 315/209 M, 209 SC; 350/582

[56] References Cited

U.S. PATENT DOCUMENTS

| | | | |
|---|---|---|---|
| 3,791,743 | 2/1974 | Cody et al. | 356/313 |
| 3,909,133 | 9/1975 | Hobsou et al. | 356/86 |
| 3,909,652 | 9/1975 | Ferre et al. | 356/313 |
| 3,977,761 | 8/1976 | Kawazu et al. | 350/582 |
| 4,037,962 | 7/1977 | Grisar et al. | 356/86 |
| 4,037,963 | 7/1977 | Grisar et al. | 356/313 |
| 4,056,783 | 10/1977 | Walters et al. | 356/313 |
| 4,296,358 | 10/1981 | Bernier | 315/209 CD |
| 4,411,524 | 10/1983 | Kremer et al. | 356/313 |
| 4,556,315 | 12/1985 | Berstermann | 356/313 |

FOREIGN PATENT DOCUMENTS

| | | |
|---|---|---|
| 2513345 | 2/1976 | Fed. Rep. of Germany . |
| 2513358 | 7/1976 | Fed. Rep. of Germany . |
| 2626233 | 3/1980 | Fed. Rep. of Germany . |
| 0012350 | 1/1982 | Japan ................................. 356/313 |
| 1043258 | 9/1966 | United Kingdom ................ 356/313 |
| 1066431 | 4/1967 | United Kingdom ................ 356/313 |
| 1444255 | 7/1976 | United Kingdom . |
| 1574032 | 9/1980 | United Kingdom . |

OTHER PUBLICATIONS

Anon., *Wire World International*, vol. 24, No. 3, May/Jun. 1982, p. 90.
Kontron Analytical Advertisement, *Anal. Chem.*, vol. 53, No. 2, Feb. 1981, p. 255A.
Nazimov et al., *J. Appl. Spectrosc.*, vol. 27, No. 6, Jun. 1978, p. 1512.

*Primary Examiner*—F. L. Evans
*Assistant Examiner*—Joel L. Harringa
*Attorney, Agent, or Firm*—Morse, Altman & Dacey

[57] ABSTRACT

An improved apparatus for the on site spectrometric analysis of metallic parts in an air gap is disclosed. The apparatus essentially comprises a probe to be positioned on the part, a mobile unit including a current-pulse generator for the probe to excite the part for analysis of its chemical composition in a direct reading optical emission spectrometer contained in the unit, and a flexible optical cable coupling the probe to the unit. The probe is designed for use on both flat and round parts, such as bars, billets, pipes, rods or wires as small as having a radius of one mm. The probe features an adjustable counter electrode, an inner sleeve serving as a contact electrode and an outer sleeve axially movable about the inner electrode and having a positioning V-groove. The probe further includes an electro-mechanical interlock to prevent accidental discharge thereof, and a self-cleaning mechanism for its sensor head. The current pulse generator, controlled by a computer, provides the probe with reliable sequential high voltage ignition pulses, each followed by a high energy discharge at remote distances and in three modes: a preburn made to clean the surface of the part and the surfaces of the electrodes, a precision carbon analysis mode to yield accurate carbon analyses in concentrations as low as 0.05% and with the same degree of accuracy, and an all key elements save carbon analysis mode to yield results with an accuracy of better than ±5%. Preferably, the mobile unit features a keyboard, a visual display and a printer to display and to record the analyzed data. Preferably, the apparatus is provided with a mobile power generator.

10 Claims, 8 Drawing Figures

SHEET A

SHEET B

MOBILE SPECTROMETRIC APPARATUS

BACKGROUND OF THE INVENTION

1. Field of the Invention

The present invention relates generally to mobile spectrometers and, more particularly, to an apparatus for the fast, precise, non-destructive testing of metals.

2. The Prior Art

Apparatus for the spectrometric analysis of the chemical composition of metallic parts, have been known for some time. In a known apparatus of this type, a plurality of spacing supports are located adjacent a vaporizing device, formed as a spark electrode, holding the spark electrode at a fixed distance from the part when positioned on the part. The radiation emitted by the metal vapor brought to luminescence by the device is transmitted to a spectroscope by a flexible optical waveguide. The waveguide is fastened to the base of a probe and its free end constitutes the sensing head which is pointed towards the plasma of the luminous metal vapor. The spectroscope is housed in a mobile unit, that also contains the energy source for the vaporizing device (see German Pat. No. 2,626,233).

It has been learned that external factors affect the operation and the range of application of such an apparatus. Specifically, factors which impair the stability of a plasma, such as the stability of a spark or of an arc, and factors which affect the transmission of the radiation from the luminous metal vapor to the sensing head, affect the operation and the range of application of such an apparatus. Thus the stability of the spark is impaired by uncontrollable air currents which can not be completely eliminated by the location of the spark electrode in a chamber alone. The transmission of the radiation is attenuated when passing through air. The attenuation depends on the wavelength of the light and increases as the wavelength becomes shorter. This known manually-operated apparatus is accordingly suitable only for the determination of components with long wavelengths. The analytical determination of components which produce radiation of short wavelengths are, therefore, usually accomplished in a laboratory with stationary equipment. In the laboratory, a sample of the part to be analyzed is studied in a protective gas atmosphere, such as an argon whereby wavelengths below 250 nm can also be determined.

Another disadvantage of this known apparatus resides in that a portion of the vaporized material itself settles on the sensing head which reduces the collection of radiation. The sensing head, therefore, must be cleaned periodically.

Besides apparatus of this kind, equipment also is known in which the spectrometric analytical apparatus is accommodated in a portable cabinet, housing the vaporizing device. A sleevelike chamber, open on one end, surrounds the device and serves as a spacing support. This apparatus is however unwieldy and requires great physical effort for handling by an operator (see the German Pat. Nos. 2,513,345 and 2,513,358). A device also is known in which an opening is provided in the rear of the electrode chamber through which gases formed are allowed to escape (see the British Pat. No. 1,444,255).

A portable apparatus for the spectrometric analysis of the chemical composition of flat metallic parts also is known, see the recently granted U.S. Pat. No. 4,411,524. As disclosed herein, a protective gas, preferably argon, is continuously admitted into the vicinity of the vaporizing portion and of the sensing head thereof so as to continuously flush both the spark electrode and the sensing head. This protective gas also enables the sensing of short-wave radiation, particularly that emitted by carbon, in the wavelength region below 250 nm by enhancing the intensity of its spectral line emission. This apparatus also features a ringlike nozzle about the spark electrode so as to direct a coolant airflow via a fan, with the counter electrode supported by a heat sink. In addition to the above features designed to stabilize the spark in the analytical gap, further stabilization of the spark is aided by the provision of a screen, preferably of boron nitride, to facilitate the controlled flushing of the flat metal surface being analyzed by the protective argon gas.

Extensive field experience has disclosed that the above apparatus, while satisfactory for most applications, has failed to provide that degree of precision reading, particularly as regards carbon content, as required to eliminate expensive sorting errors in the mill or in the yard. Part of this problem has been traced to the presence of objectionable matter on the surface of the metallic part, such as rust or the like. It has also been noted that the presence of an auxiliary spark gap in the pulse generator further destabilized the apparatus, again adversely affecting readings. Such auxiliary spark gaps are inherently unstable, requiring frequent adjustments and cleaning. Additionally, auxiliary spark gaps remain sensitive to atmospheric conditions, such as moisture and temperature, which adversely affect the use of analytical apparatus incorporating such pulse generators. Further, the above apparatus per U.S. Pat. No. 4,411,524 is limited to analyzing flat metallic parts only. It cannot properly be used to sort and analyze round metallic parts, such as welding wire or the like.

SUMMARY OF THE INVENTION

It is a principal object of the present invention to overcome the above disadvantages by providing an improved portable apparatus for the on site, rapid, precision, non-destructive testing of metallic parts in the mill or in the yard.

More specifically, it is an object of the present invention to provide an apparatus for the precision spectrometric analysis of the chemical composition of metallic parts, whether flat or round, in an air gap (i.e., without the use of any protective gas, such as argon) and characterized by improved stability in its spark. The apparatus of the invention essentially comprises a probe designed to be placed on the metallic part and having a device for vaporizing the part, the probe featuring: a unique structure designed not only to maintain the size of the analytical gap constant but also properly to position the same with respect to round metallic parts (i.e., perpendicular to its round surface), including bars, pipes, rods and wires as thin as having a one mm radius; a further structure designed for intermittently and physically cleaning the head of the sensing means of the emitted radiation by the vaporized part; and an electro-mechanical interlock designed to prevent accidental discharge through the analytical gap. The apparatus further includes a mobile unit incorporating a unique and stable excitation source for the probe, unaffected by atmospheric conditions, providing reliable sequential high voltage ignition pulses, followed by high energy discharges at remote distances and in three operative modes: a preburn mode to clean the surface of the part to be analyzed and the surfaces of the elctrodes; a precision carbon analysis mode, using a specific emission line of carbon, yielding carbon analyses in concentrations as low as 0.05% and with the same degree of accuracy: and an all key elements save carbon analysis mode to yield results with an accuracy of better than ±5%. The excitation source preferably is under the control of a computer, preferably a 16-bit microprocessor with a 5 MHz cycle time, including a non-volatile memory. A flexible optical cable, that can be ten to twelve meters or so in length, connects the probe to the mobile unit. This cable length allows the operator to analyze and/or to sort many samples without having to move the mobile unit. Preferably, the mobile unit includes a direct reading optical emission spectrometer of temperature compensating design and with a wavelength coverage from about 190.0 to about 440.0 nm, a voltage regulator, a touch sensitive membrane keyboard, a visual display unit, and a printer to record the analyzed data. Preferably, the apparatus is provided with a mobile power generator to allow its use even in yards having no conventional power outlet.

Other objects of the present invention will in part be obvious and will in part appear hereinafter.

The invention accordingly comprises the spectrometric apparatus of the present disclosure, its components, parts and their interrelationships, the scope of which will be indicated in the appended claims.

BRIEF DESCRIPTION OF THE DRAWINGS

For fuller understanding of the nature and objects of the present invention, reference is to be made to the following detailed description, which is to be taken in connection with the accompanying drawings, wherein.

DETAILED DESCRIPTION OF THE PREFERRED EMBODIMENT

Figure 1:
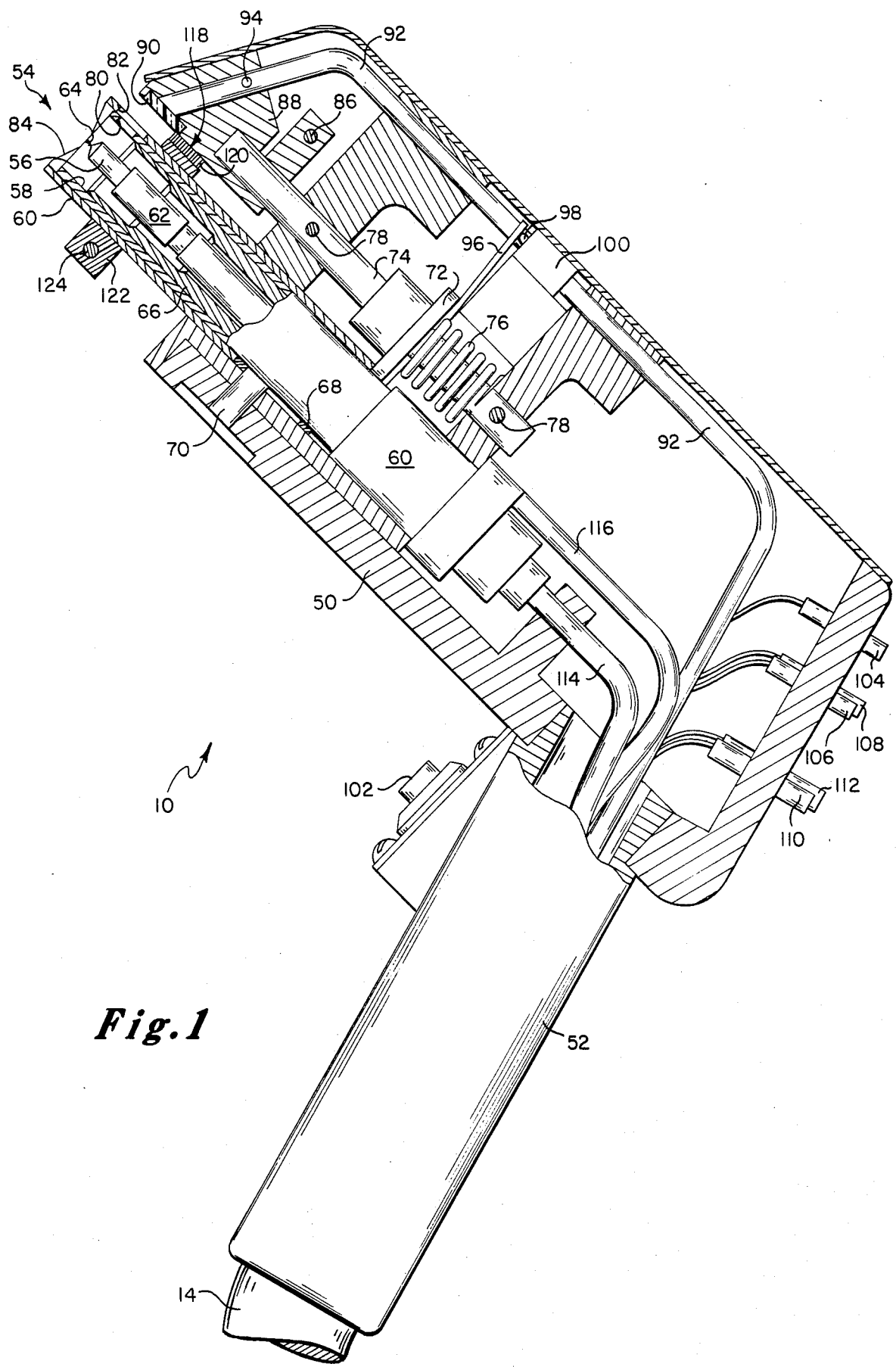
FIG. 1 is a view, in side elevation and partly in axial section, of one operative part of an apparatus constructed in accordance with the present invention.
Figure 3:
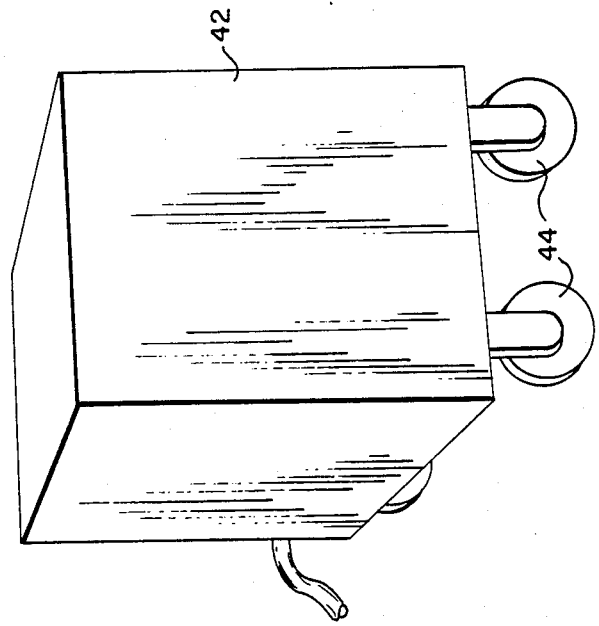
FIG. 3 is a perspective view of still another optional operative part of the apparatus according to the invention.
Figure 2:
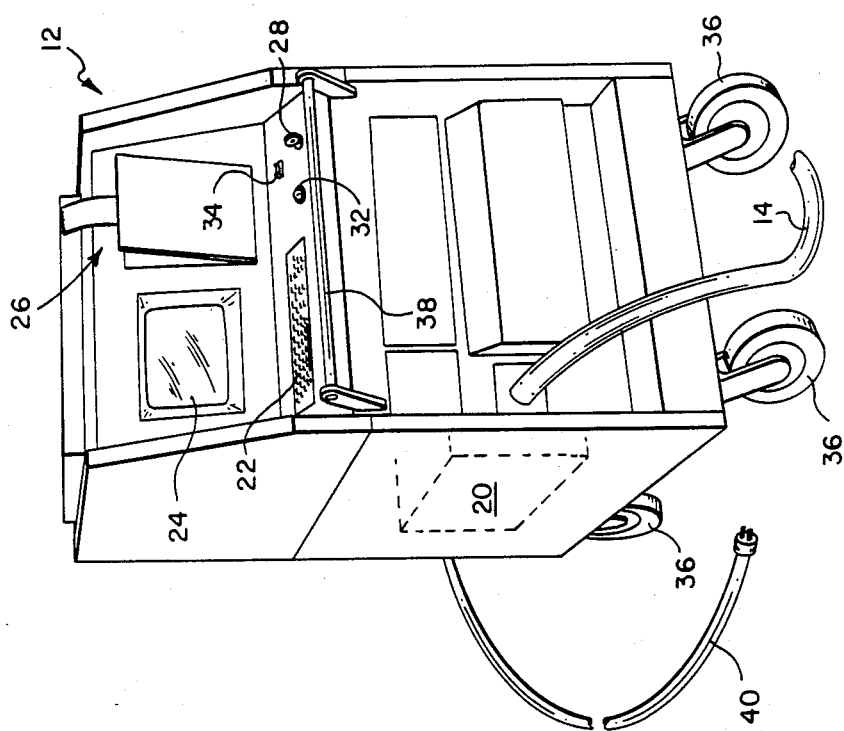
FIG. 2 is a perspective view of another operative part of the apparatus according to the invention.

In general, the illustrated preferred embodiment of an improved apparatus for the on site spectrometric analysis of the chemical composition of metallic parts, whether flat or round, in an air gap essentially comprises a probe 10 shown in FIG. 1, a mobile unit 12 shown in FIG. 2, and a flexible optical cable 14, shown partly in FIG. 1 and in FIG. 2, coupling the probe 10 to the unit 12. The apparatus, among others, is characterized by improved stability in its spark under all atmospheric conditions and that without the employment of a protective gas such as argon, in the vicinity of the analytical gap and of the sensing head.

The probe 10 is designed to allow for the on site spectrometric analysis of both flat and round metallic parts, including bars, billets, pipes, rods, welding wires and the like, including wires as small as having a radius of but one millimeter.

Figure 4:
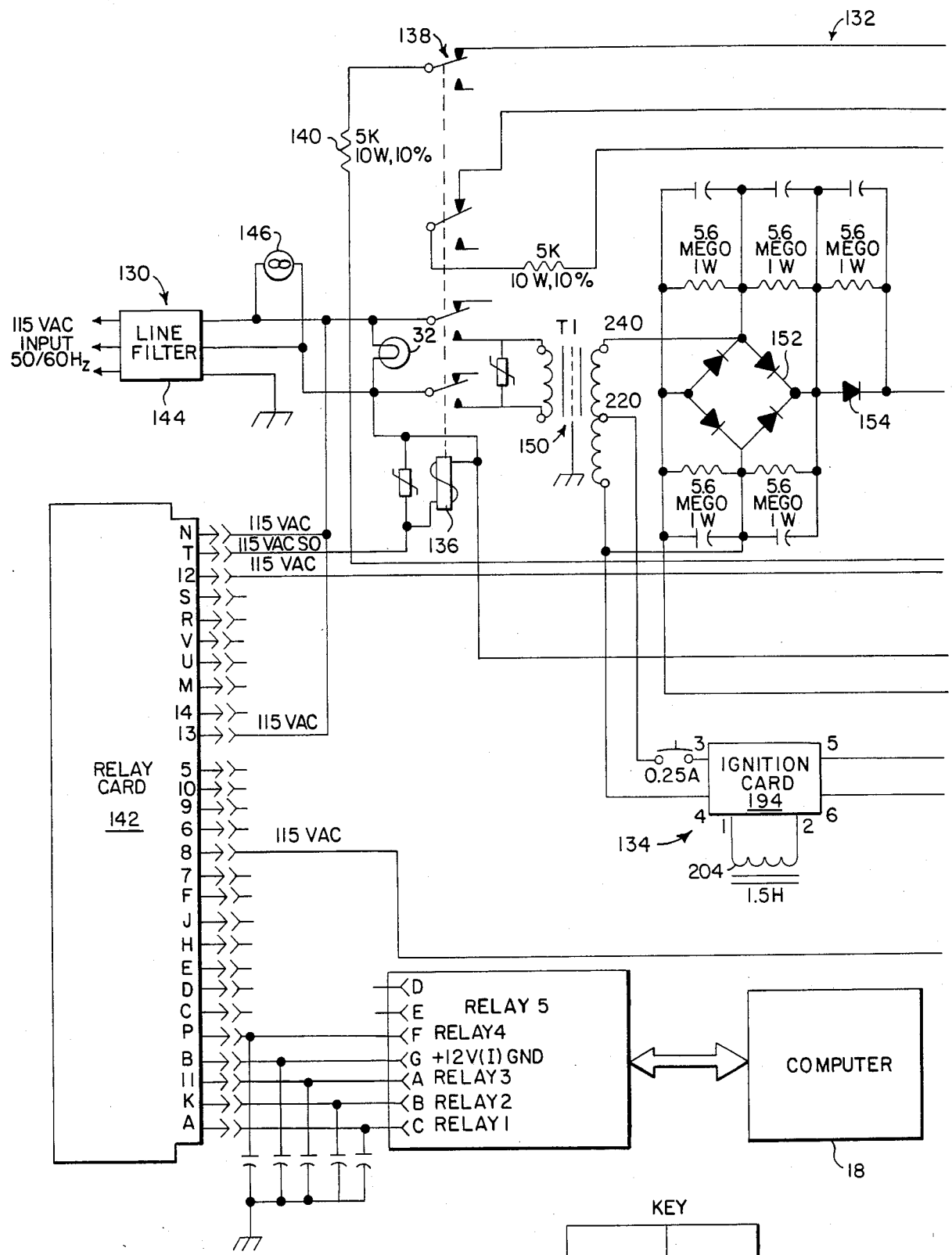
FIG. 4 is a schematic diagram, partly in block form, of a pulse generating source for the part shown in FIG. 1.
Figure 4:
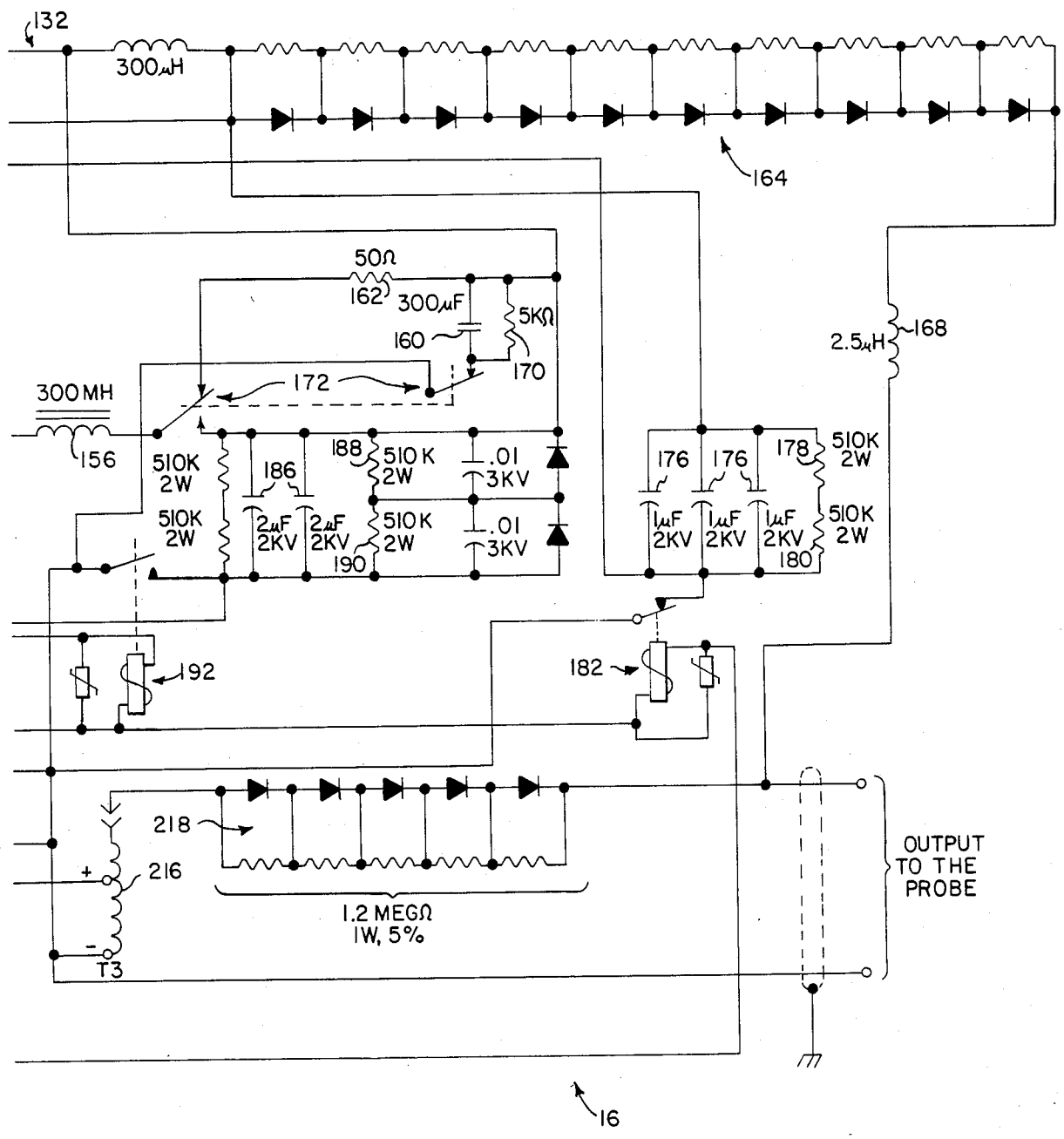

An improved excitation source 16 for the probe 10 is shown in schematic and partly in block form in FIG. 4. The excitation source is stable due to its construction and exhibits no adverse sensitivity to atmospheric changes, such as regards moisture and temperature. The source 16 generates and transmits to the probe 10 reliable sequential high voltage ignition pulses, in excess of 3 KV, to ionize the air (i.e., atmospheric) analytical gap, followed by sequential high energy discharges therethrough (at least about 0.72 Joule) at remote distances (about ten to twelve meters) and in three operative modes for the probe 10: a preburn mode to clean the surface of the metallic part to be analyzed in the vicinity of the air analytical gap as well as to clean the surfaces of the electrodes; a precision carbon analysis mode (carbon being the most critical alloy in steel), using a specific emission line of carbon, i.e., 2296.8 Angstroms, yielding carbon analyses in concentrations as low as 0.05% and with a consistent 0.05% degree of accuracy; and an all key elements, alloys and residuals, excepting carbon, analysis mode to yield results with an accuracy of better than ±5%.

Specifically, the precision carbon analysis mode is effected as follows. Simultaneously with the measurement of the carbon intensity at 2296.8 Angstroms, a background measurement of the light intensity of a three Angstroms spectral range centered about 2280 Angstroms is taken. Empirical research yielded that when this non-standard spectral range is used for background, improved results were obtained over those using the conventional iron emission lines of 2714 or 3227 Angstroms. Then, the carbon intensity measurement at 2296.8 Angstroms is divided by the background intensity measurement at 2280 Angstroms and the quotient is used to calculate the precise carbon concentration. As a result, variations from burn-to-burn are compensated for, giving a more precise analysis.

The excitation source 16 preferably is under the control of a computer 18. Computer 18 preferably is at least a 16-bit microprocessor, with a 5 MHz cycle time and including a non-volatile memory, such as exemplified by the "Falcon SBC 11/21" model computer made by the Digital Equipment Corporation, Maynard, Mass.

The mobile unit 12, in addition to housing the excitation source 16 and the computer 18, also includes a spectrometer 20. Preferably, the spectrometer 20 is a direct reading optical emmission spectrometer of temperature compensating design, with a focal length of 75 cm, a 0.55 nm/mm dispersion, and having a wavelength coverage from about 190.0 nm to about 440.0 nm. Preferably, the spectrometer is provided with anywhere up to twenty-one channels, and includes a mercury alignment monitor. The mobile unit 12 also is provided with a keyboard 22, a visual display unit 24, a printer 26, an emergency stop button 30, a power-on indicator light 32, and a printer-on-off switch 34. Preferably, the keyboard 22 is a touch-sensitive membrane keyboard, ideal for industrial environments, a design which prevents problems that occasionally arise with conventional pushbutton keyboard designs. The visual display unit 24 preferably includes a nine inch cathode ray tube that displays information in easy-on-the-eye green on a black background. The computer 18 preferably is programmed so that in response to a keyboard input of "HELP," it displays a menu of programs, including "AUTO SORT" to check whether all metallic parts in a particular lot are of the same quality; "SORT" in which the desired elements and their respective ranges are selected in advance, with minimum and maximum levels established for each one element; and "ANALYZE" in which elements of interest in each metallic part are "read" with an accuracy of better than ±5% of the amount of the particular element present, save for carbon content, which is read with an accuracy of about 0.05%. The results of the different readings are promptly displayed on the CRT tube. If the operator wishes, he may at any time call for a display of a summary report. The printer 26, when engaged, provides a permanent record of the readings taken. Preferably, the mobile unit 12 is provided with a plurality of casters 36 and a handle 38 by means of which it can be moved from one job site to the next. Further, the unit 12 is provided with a power cable 40 designed to be plugged into a conventional 110 VAC, 50 Hz power outlet. A separate 2 KW power generator unit 42 is provided for locations where no conventional power is available. The power generator unit 42 preferably also is mounted on a plurality of casters 44 and features a flexible power connector 46 designed to work with the power cable 40 of the mobile unit 12. Each of the above described units of the mobile spectrometric apparatus is designed for operation under most environmental conditions, including a temperature range from about −18° C. to about 50° C. (0°–120° F).

DETAILED DESCRIPTION OF THE PROBE OF FIG. 1

The probe 10 of the mobile spectrometric apparatus of the invention is illustrated in side elevation and partly in axial section in FIG. 1. The probe 10 preferably is formed with an exterior shape suggestive of a hand-held gun; hence it is customarily referred to in the trade as the "spark gun." The proble 10 basically includes a housing 50 and a handle 52 to which the flexible optical cable 14 is connected. The housing 50 and the handle 52 may be formed of metal; preferably however, they are formed of a hard plastic material, as for example by injection forming.

The housing 50 supports at its forward end a vaporizing means 54. The vaporizing means 54 comprises a central counter electrode 56, an inner sleeve 58 serving as a contact electrode, and an outer sleeve 60. The central counter electrode 56 is mounted, axially adjustably, within a member 62. By being axially adjustable, the distance 64 between the tip of the counter electrode 56 and the end of the inner sleeve 58, preferably set at the factory and representing the analytical gap, also can be readjusted in the field, as needed. The inner sleeve 58, on the other hand, is fixedly secured within the housing 50. An insulating sleeve 66 is secured along most of the axial length of the inner sleeve 58. The outer sleeve 60 is mounted for axial displacement about the inner sleeve 58. The extent of its axial travel is determined by the length of an axial slot 68 cut into the sleeve 60 and a thereto projecting alignment pin 70, whose diameter is such as to snugly fit within the slot 68. Consequently, the outer sleeve 60 can only move axially but not radially with respect to the inner sleeve 58. A switch actuating member 72 is freely disposed about a rod 74, but is normally urged forward by a compression spring 76. The rod 74 is mounted in spaced parallel relation to the vaporizing means 54 and is conveniently secured to the housing 50 by a pair of set screws 78.

Both sleeves 58 and 60 are provided with windows 80 and 82, respectively, with the window 82 of the outer sleeve 60 being larger than the window 80 in the inner sleeve 58. The outer sleeve 60 further is formed with a V-groove 84, the significance of which will become apparent from below. Preferably, V-groove 84 is formed with an obtuse angle, from about 95° to about 105°.

Adjacent the windows 80 and 82 and on the forward end of the rod 74 is secured, via a suitable cap screw 86, a holder member 88 for a sensor head 90 of an optical waveguide cable 92, secured within the holder member 88 by a set screw 94.

The switch actuating member 72 is designed to bear against a flat spring 96, one end of which is attached thereto. When flexed, the free end of the flat spring 96 will actuate a pin 98 of a micro switch 100. Preferably, the switch 100 is a snap-action switch. A starter switch 102 is mounted in the grip of the handle 52. In order to operate the probe 10 by initiating any discharge between the electrodes 56 and 58, it is necessary for both switches 100 and 102 to be actuated. Switch 100 is actuated by the outer sleeve 60 being pressed against a sample to be analyzed, thereby sliding the outer sleeve 60 backward. The sliding outer sleeve 60 in turn moves the switch actuating member 72 backward on the rod 74. Member 72 now flexes the flat spring 96, which in turn actuates the pin 98 of the switch 100. At this point, if the operator also depresses with his finger the starter switch 102, the probe 10 will fire, as intended. The probe 10 will continue operating as long as both switches 100 and 102 remain engaged. By this electro-mechanical interlock between the two switches 100 and 102, accidental discharge between the electrodes 56 and 58 effectively is prevented.

The back of the probe housing 50 preferably is provided with a green light 104 to signal "GO/MATCH," a yellow light 106 to signal "BAD DATA/NO MATCH," and a red light 108 to signal "BAD BURN," and a pair of buttons 110 and 112, the former marked "PRINT" to actuate the printer 26 on the mobile unit 12, and the latter marked "RESET," which is to be actuated before starting a new reading. Electrical power is coupled to the counter electrode 56 via a hot lead 114, with a return lead 116 completing the circuit back to the source.

The probe 10 further is provided with means 118 for intermittently cleaning the sensor head 90 in between samplings. Means 118 comprises a wiper brush 120, which is secured to a holder 122, as for example by being glued thereto. The holder 122 in turn is detachably secured, by means of a set screw 124, about the outer periphery of the outer sleeve 60.

DETAILED DESCRIPTION OF THE EXCITATION SOURCE MEANS OF FIGS. 4–5

Figure 5:
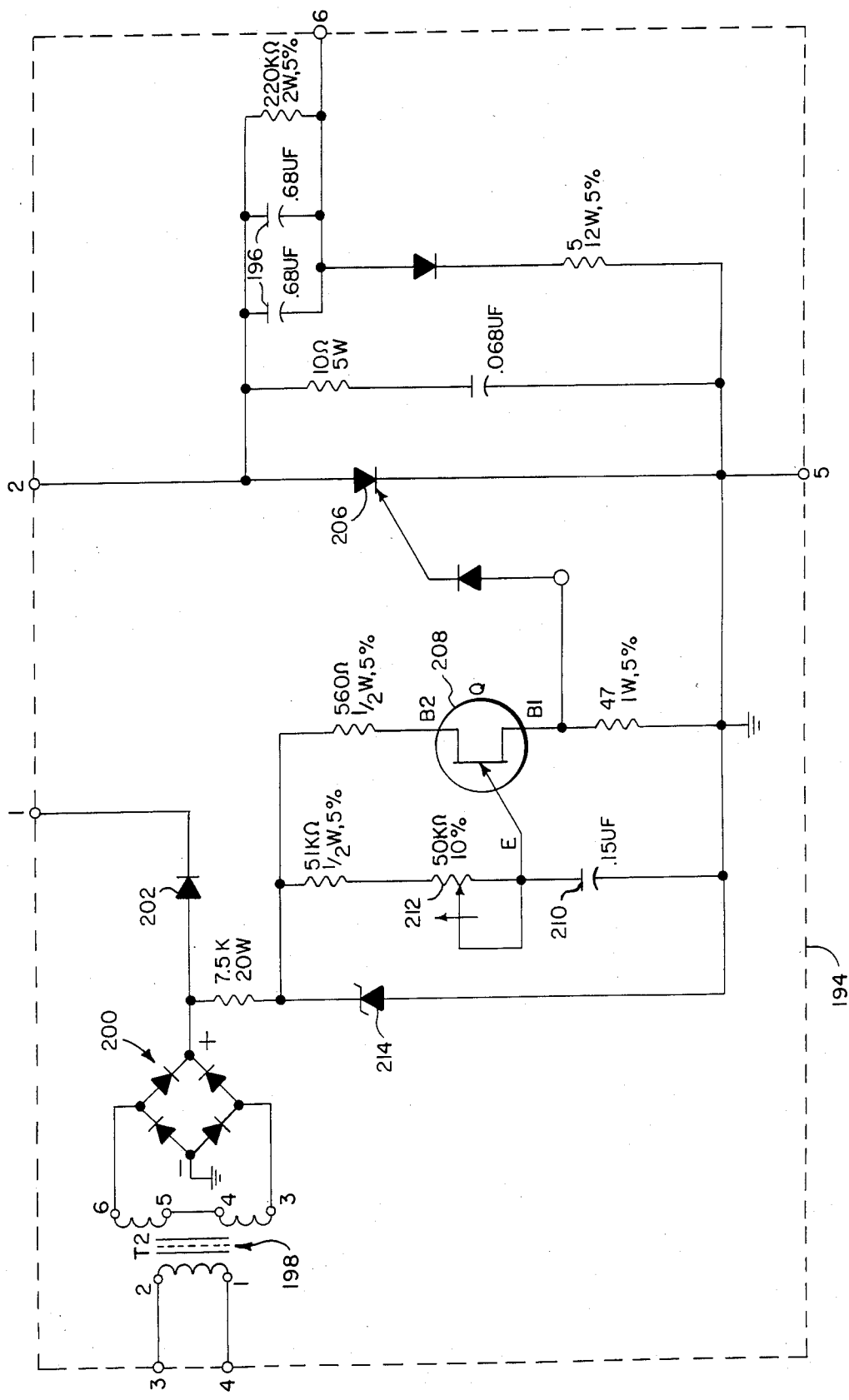
FIG. 5 is a schematic diagram of a portion of the pulse generating source illustrated in block form in FIG. 4.

The excitation source means 16 for the probe 10 is contained within the mobile unit 12 and is disclosed schematically in FIGS. 4 and 5. Essentially, the excitation source 16 comprises a power circuit 130, powering a pulse forming network (PFN) 132 and an ignition circuit (IC) 134. The excitation source 16, under the control of the computer 18, provides the probe 10 with reliable sequential high-voltage ignition pulses from the IC 134, followed by high energy discharges at remote distances (i.e., with the probe 10 being removed by ten meters or more from the mobile unit 12) and in three distinct operative modes for the probe 10: a preburn mode (PB-M) thoroughly to clean the surface of the metallic part prior to it being tested as well as to clean the surfaces of the electrodes; a precision carbon analysis mode (CM), to yield accurate carbon analyses in concentrations as low as 0.05% and with the same degree of accuracy; and an all key elements save carbon analysis mode (AESC-M) to yield results with an accuracy of better than ±5%.

Power for the excitation source 16 is controlled by a power contactor 136, closing its normally open plurality of contacts 138 and removing a bleeder safety resistor 140 from across the PFN 132, and by a relay card 142. Preferably, power to the excitation source means 16 is admitted via a suitable line filter 144. Its presence is signalled by the power-on indicator light 32. A cooling fan 146 preferably is provided to keep the power circuit 130 from overheating. The coil of the power contactor 136 is in an interlocked start/stop circuit with the switches 100 and 102 of the probe 10 to guard against accidental discharge of the excitation source means 16 via the probe 10 with no sample being present.

Power first is applied to an isolation step-up transformer 150, whose secondary is tapped respectively to power both the PFN 132 and the IC 134. Power to the PFN 132 is via a full wave bridge 152, whose positive output is fed through a silicon rectifier 154 and a charging inductor 156.

The pulse forming network (PFN) 132 is designed to generate, seriatim, three diffferent types of discharges in each of the three above-mentioned operative modes of the probe 10. Namely, first a high energy DC arc discharge in the preburn mode via a circuit which includes a high capacitance capacitor 160 (preferably about 300 uF), a resistor 162, a string of unidirectional devices 164 (preferably diodes), and a low inductance coil 168. Preferably and for safety reasons, a high resistance path is formed across the capacitor 160 by a resistor 170 to dissipate any charge remaining on the capacitor within a fraction of a second after the circuit is disconnected. Connection to this circuit preferably is effected via a two-pole relay 172.

Figure 7:
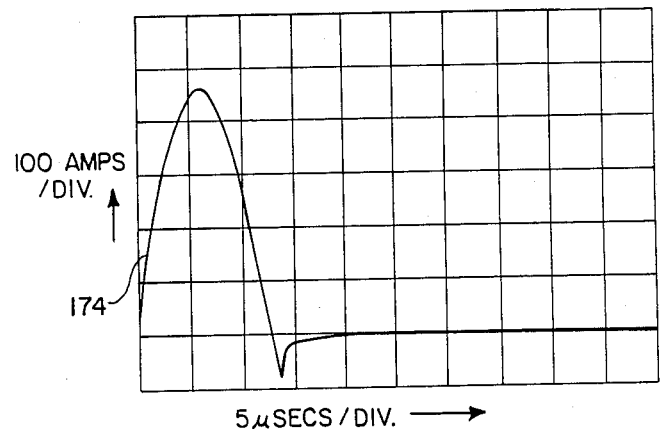

The second type of discharge generated by the PFN 132 is a unidirectional high current, short duration spark discharge pulse applied in the precision carbon analysis mode. A representative current waveform 174 of such a unidirectional high current, short duration spark discharge pulse is illustrated in FIG. 7. The circuit responsible for generating this pulse includes a capacitor bank comprising three parallel-coupled capacitors 176, shunted by a pair of high value resistors 178 and 180, provided for safety so as again to dissipate any charge remaining on the capacitor bank after power to this circuit is disconnected. Power to this circuit for charging the capacitors 176 is coupled thereto via a relay 182. The capacitors 176 are discharged through the string of diodes 164 and the coil 168 into the probe 10 and thereby across the analytical gap as represented by the fixed distance 64 between the tip of the counter electrode 56 and the outer sleeve 58, as shown in FIG. 1. It is again pointed out that the analytical gap is simply an air gap, i.e., there is no protective gas, such as argon, present in the analytical gap at any time during the operation of the probe 10.

Figure 8:
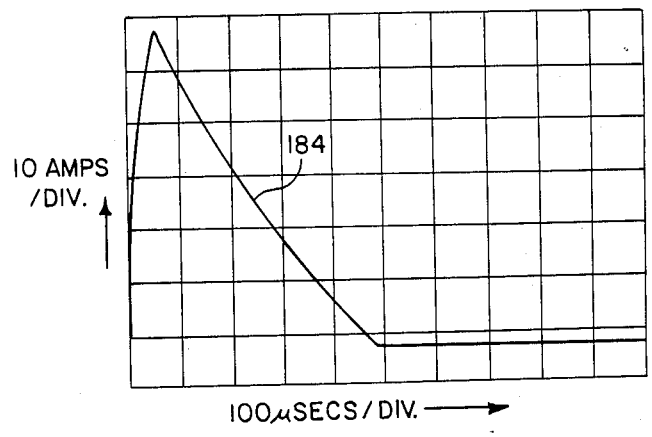

The third type of discharge generated by the PFN 132 is an arc-like low current discharge pulse applied in the selected key elements save carbon analysis mode. A representative current waveform 184 of such an arc-like low current discharge pulse is illustrated in FIG. 8. The circuit responsible for generating this pulse includes a third capacitor bank comprising two parallel-coupled capacitors 186, also preferably shunted by a pair of bleeder resistors 188 and 190. Power to this circuit for charging the capacitors 186 is coupled thereto via a relay 192. The capacitors 186 are discharged first through a high inductance coil of 300 H, hence via the string of diodes 164 and the low inductance coil 168 into the probe 10, and thereby across the analytical air gap of the vaporizing device 54.

Before discharge of any one of the above three current pulses through the analytical air gap of the vaporizing device 54 can take place, the analytical air gap must first be ionized. The ionization function is achieved by the ignition circuit (IC) 134. Heretofore known ignition circuits also included an auxiliary gap. Consequently, such prior art circuits inherently included most of the undesirable features associated with auxiliary gaps such as: the lack of stability, the requirement for frequent adjustments, the requirement for frequent cleaning, and the sensitivity to atmospheric changes such as moisture and temperature. This resulted in a lack of precision, consistency and reliability of the readings taken by the instrumentation using an auxiliary gap in the ignition circuit.

The ignition circuit (IC) 134 of the invention does not include an auxiliary gap. Hence, it is more stable than known ignition circuits. The IC 134 includes an ignition card 194 (see FIG. 5) which comprises a pair of ignition capacitors 196 being charged via a transformer 198, a full wave bridge 200, a second silicon rectifier 202 and a second charging coil 204 (see FIG. 4). Power to transformer 198 is taken from the secondary of the transformer 150. The ignition capacitors 196, upon being fully charged, are discharged when a silicon controlled rectifier (SCR) 206 is rendered conductive by a trigger pulse applied to its gate. The trigger pulse is generated by a unijunction transistor 208 of a unijunction trigger circuit that further includes a capacitor 210 and a variable resistor 212 whose setting determines the time interval for the firing of the transistor 208 so as to generate the trigger pulse for the SCR 206. The supply voltage for the unijunction trigger circuit also is taken from the positive terminal of the full wave bridge 200 and is preferably clipped to a preset level by a Zener diode 214.

The ignition capacitors 196 are discharged into the primary of an ignition transformer 216. The ignition transformer 216 is coupled via a string of unidirectional devices 218 to the probe 10, specifically to the hot lead 114 thereof leading to the counter electrode 56.

Figure 6:
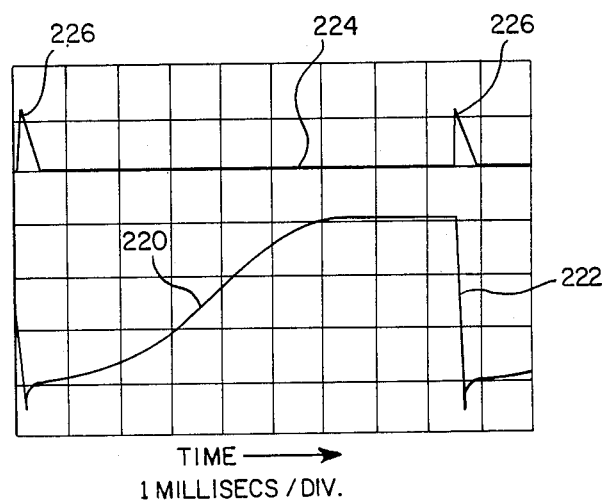
FIGS. 6-8 illustrate certain representative waveforms helpful in understanding the invention.

In FIG. 6, there is illustrated, first a curve 220 representing the voltage across the capacitors 186 while they are being charged and a spike 222 at the point when the capacitors 186 are discharged into the analytical gap. A further waveform 224, with periodic spikes 226, illustrates the operation of the ignition circuit (IC) 134. It is to be observed that the ignition pulses, represented by the spikes 226, which ionize, i.e., break down the analytical gap, occur late in the capacitor charging cycle, at least about two milliseconds after the capacitors 186 have been fully charged. These ignition pulses 226 from the IC 134, which ionize and thus break down the analytical gap and initiate seriatim, each one of the three types of discharges from the PFN 132, are high voltage ignition pulses, preferably in excess of 3 KV.

OPERATION OF THE APPARATUS OF THE INVENTION

First, the operator selects the type of job to be done, all displayed for selection on the visual display unit 24. Following the step-by-step instructions also displayed on the unit 24, the operator places the vaporizing device 54 of the probe 10 firmly against the metallic part to be analyed. If the metallic part is flat, the vaporizing device 54 will assume the position illustrated in FIG. 1, with the outer sleeve 60 sliding backward until its end is flush with the stationary inner sleeve 58. At that point, two significant events have been effected: first, the size of the analytical gap 64 between the part to be analyzed and the counter electrode 56 has assumed its predetermined fixed distance and, second, the sliding outer sleeve 60 has triggered the safety micro-switch 100, enabling the electro-mechanical interlock in the excitation source 16 so that the source 16 can be activitated upon the operator depressing the starter switch 102 with his finger.

If the metallic part is a round object, such as a welding wire and has at least a radius of one mm, the wire will be placed within the V-groove 84 and the probe 10 pressed against the wire until the surface of the wire will have assumed its predetermined fixed distance, i.e., the size 64, from the tip of the counter electrode 56. Additionally, the V-groove 84 of the sliding outer sleeve 60 also assures that the axis of the counter electrode 56 is positioned precisely perpendicular to the curved surface of the metallic wire being sampled.

When the operator depresses the starter switch 102, the computer 18 takes over and effects the discharges, seriatim, of the three types of current pulses through the analytical gap. During the preburn mode, the surface of the sample as well as the electrode surfaces are cleaned. During the next succeeding two operative modes of the probe 10, radiation generated by sample excitation in the analytical gap is directed to the photomultiplier tubes (PM's) of the spectrometer 20 and is quantized and converted to meaningful information (either % concentration; match/no match, etc.) by the computer 18 and its associated circuitry. Sampling time usually takes from about two to six seconds, affected largely by the condition of the sample, as when requiring more than one preburn cycle for cleaning its surface.

The spectrometer 20 of the apparatus of the invention has been designed to detect and measure, for carbon content in the precision carbon analysis mode, a specific emission line of carbon, namely the one occuring at a wavelength of 2296.8 Angstroms. It is as a consequence of empirical investigation of trial and error which yielded a combination of the use of this specific emission line of carbon, together with the utilization of the high current, unidirectional, short duration spark discharge, which enabled the apparatus of the invention to achieve the precision carbon content analysis to 0.05% accuracy in an air (i.e., atmospheric, with no protective gas, such as argon, being present) analytical gap. This accuracy is achieved in carbon content concentrations even at such low ranges as from about 0.05% to about 1.5% and with good repeatability.

Thus it has been shown and described an improved apparatus for the on site spectrometric analysis of metallic parts in an air gap, which apparatus satisfies the objects and advantages set forth above.

Since certain changes may be made in the present disclosure without departing from the scope of the present invention, it is intended that all matter described in the foregoing specification or shown in the accompanying drawings be interpreted in an illustrative and not in a limiting sense.

What is claimed is:

1. Apparatus for the spectrometric analysis of metallic parts in an air gap comprising:
   (a) a probe designed to be positioned on a metallic part and provided with means for vaporizing said part, said probe including means for spacing and positioning said probe on said part, said spacing determining said air gap, means for sensing radiation of metallic vapor vaporized by said vaporizing means, means to control the operation of said probe, and means for intermittently cleaning said sensing means;
   (b) a mobile unit including excitation means for said probe, said excitation means designed to operate said probe in three modes: a preburn mode, a precision carbon analysis mode, and an all other elements save carbon anlysis mode, and computer means to control the operation of said excitation means; and
   (c) a flexible optical cable coupling said probe to said mobile unit;
   (d) said vaporizing means comprising an adjustable counter electrode, an inner sleeve serving as a contact electrode concentrically and fixedly mounted about said counter electrode, and an outer sleeve axially movable about said inner sleeve, said sleeves provided with windows, said windows being at least partly superimposed one over the other and adjacent said sensing means when said vaporizing means vaporizes said part;
   (e) said spacing and positioning means for said probe on said part including said adjustable counter electrode and said sleeves, and a V-groove formed in said outer sleeve and designed to space and position round metallic parts, said round metallic parts having radii from about one mm to about one cm;
   (f) said means to control the operation of said probe including a pair of switches, one of said pair of switches being actuable by an operator's finger and the other of said pair of switches being actuable by said spacing and positioning means.

2. The apparatus of claim 1 wherein said other of said pair of switches comprises a snap action switch and a flat spring operatively mounted thereagainst and spring-biased means for actuating said flat spring to actuate said snap action switch, said spring-biased means operable by the displacement of said outer sleeve over said inner sleeve.

3. The apparatus of claim 1 wherein said means for intermittently cleaning said sensing means comprises a wiper assembly mounted about said axially movable outer sleeve and provided with a wiper brush, said wiper brush having two operative positions: one adjacent and contacting said sensing means and a second free of said sensing means.

4. The apparatus of claim 1 further including a mobile power generator for providing on site power for said apparatus to render the same independently operable.

5. The apparatus of claim 1 wherein said excitation means comprises a pulse forming network and an ignition circuit, said pulse forming network to generate three different types of discharge at remote distances in each of said three operative modes: a high energy DC arc discharge in said preburn mode, a high current, short duration spark discharge in said precision carbon analysis mode, and a low current discharge in said all element save carbon analysis mode.

6. The apparatus of claim 5 wherein said ignition circuit includes ignition capacitors, an ignition transformer coupled thereto, triggering means to discharge said ignition capacitors into said ignition transformer, and a string of unidirectional devices connected in series between said ignition transformer and said probe.

7. The apparatus of claim 5 wherein said pulse forming network comprises three separate capacitor banks for each of said three operative modes: a high capacitance capacitor bank for said preburn mode and low capacitance capacitor banks for the other two operative modes, each of said three separate capacitor banks being charged seriatim via a charging inductor and being discharged seriatim so as to sequentially excite said probe, the discharge paths in said preburn mode and said precision carbon analysis mode including a string of unidirectional devices and a low inductance coil and in said all element save carbon analysis mode further including a high inductance coil connected between said capacitor bank and said string of unidirectional devices.

8. The apparatus of claim 6 wherein said triggering means comprises a unijunction trigger circuit including a unijunction transistor for generating a trigger pulse to actuate a device, said device being coupled to said ignition capacitors for producing an ignition discharge, and wherein in said precision carbon analysis mode of operation, a specific short-wave spectral emission line of carbon below 250 nm is used in said radiation sensing means so as to yield carbon analysis of said metallic part in concentrations ranging from about 0.05% to about 1.5% with an accuracy of about 0.05% per spectrometric analysis, said ignition discharge being a high voltage discharge in excess of 3 KV so as to ionize said air gap between said vaporizing means and said metallic part.

9. A probe for use in spectrometric apparatus and designed to be positioned on a metallic part to be analyzed, said probe comprising:
  (a) means for vaporizing said part including a counter electrode and a sliding sleeve-fixed sleeve arrangement concentrically mounted about said counter electrode designed to maintain said part at a fixed distance from said counter electrode;
  (b) means for preventing accidental use of said probe including a switch and a spring member mounted in operative association with said sliding sleeve-fixed sleeve arrangement, said switch being actuable by said sliding sleeve when said probe is positioned on said part;
  (c) means for sensing radiation of metallic vapor of said part vaporized by said vaporizing means;
  (d) means detachably mounted on said sliding sleeve-fixed sleeve arrangement for intermittently cleaning said sensing means; and
  (e) a V-groove formed in said sliding sleeve and designed to space and to position metallic parts formed as round objects, such as wires having a radius of at least about one mm, and windows provided in said sliding and fixed sleeves in operative association with said sensing means and wherein said means for intermittently cleaning the sensing means includes brush means removeably secured thereto.

10. An excitation means for use in an apparatus for the spectrometric analysis of metallic parts comprising:
  (a) a power circuit including an isolation step-up transformer, a full wave bridge, a silicon rectifier and a charging coil;
  (b) a pulse forming network coupled to said charging coil of said power circuit and including three individually chargeable capacitor banks, two of said capacitor bands being dischargeable into a load through a string of unidirectional devices and a low inductance coil and the third of said capacitor banks further including in said discharge path a high inductance coil coupled between said string of unidirectional devices and said bank;
  (c) an ignition circuit coupled to said isolation step-up transformer and designed to generate, seriatim, ignition pulses to permit said three capacitor banks to be discharged, seriatim, into said load, said ignition circuit including ignition capacitors, and ignition transformer coupled to said ignition capacitors, and a string of unidirectional devices connected in series between said ignition transformer and said load; and
  (d) a unijunction trigger circuit and a silicon controlled rectifier to initiate the discharge of said ignition capacitors into said ignition transformer.

* * * * *